(12) United States Patent
Cattaneo et al.

(10) Patent No.: US 9,668,893 B2
(45) Date of Patent: *Jun. 6, 2017

(54) INTRAVASCULAR FUNCTIONAL ELEMENT AND SYSTEM FOR SUCH A FUNCTIONAL ELEMENT (71) Applicant: Admedes Inc, Livermore, CA (US)

(72) Inventors: Giorgio Cattaneo, Karlsruhe (DE); Werner Mailänder, Engelsbrand Grunbach (DE)

(73) Assignee: Admedes Inc., Livermore, CA (US)

( * ) Notice: Subject to any disclaimer, the term of this patent is extended or adjusted under 35 U.S.C. 154(b) by 103 days.

This patent is subject to a terminal disclaimer.

(21) Appl. No.: 14/177,471

(22) Filed: Feb. 11, 2014

(65) Prior Publication Data

US 2014/0228935 A1 Aug. 14, 2014

(30) Foreign Application Priority Data

Feb. 11, 2013 (DE) .................. 10 2013 101 337

(51) Int. Cl.
*A61F 2/06* (2013.01)
*A61F 2/86* (2013.01)
(Continued)

(52) U.S. Cl.
CPC .................. *A61F 2/86* (2013.01); *A61F 2/90* (2013.01); *A61L 31/022* (2013.01); *A61L 31/088* (2013.01)

(58) Field of Classification Search
CPC ...... A61F 2/86; A61F 2/04; A61F 2/88; A61F 2/90; A61L 31/022; A61L 31/088;
(Continued)

(56) References Cited

U.S. PATENT DOCUMENTS 3,643,658 A 2/1972 Steinemenan
6,110,204 A 8/2000 Lazarov et al.
(Continued)

FOREIGN PATENT DOCUMENTS

CH 497891 10/1970
DE 19506188 8/1996
(Continued)

OTHER PUBLICATIONS

German Office Action dated Sep. 19, 2013 for the Corresponding German Patent Application No. DE 10 2013 101 337.6.
(Continued)

*Primary Examiner* — Katherine M Shi
(74) *Attorney, Agent, or Firm* — Hassan Abbas Shakir; Katten Muchin Rosenman LLP (57) ABSTRACT The invention relates to an intravascular functional element with a tubular grid structure (12) that has a wire (10) or several wires (10) respectively of an alloy with nickel and titanium as alloying elements, wherein a mixed oxide layer with a layer thickness of 15 nm to 100 nm and containing $TiO_2$ and at least one nitride, especially titanium oxynitride and/or titanium nitride, is formed on the surface of the wire or on the surface of the wires (10)/of the wires (10), wherein the grid structure forms cells of mutually crossing wires (10) or wire segments of the wire (10) in longitudinal direction and in circumferential direction respectively and in circumferential direction there are disposed at least 6 cells, especially at least 12 cells, especially at least 16 cells, especially at least 24 cells, especially at least 36 cells, especially at least 48 cells.

16 Claims, 6 Drawing Sheets (51) Int. Cl.
*A61L 31/02* (2006.01)
*A61L 31/08* (2006.01)
*A61F 2/90* (2013.01)

(58) Field of Classification Search
CPC .. A61L 2400/18; A61L 27/306; A61L 29/106; A61L 31/14; C23C 14/0676; C23C 28/04; C23C 30/00
USPC ........... 623/1.11, 1.15, 11.11, 1.46; 148/421, 148/426; 427/126.3, 2.24, 456, 2.21
See application file for complete search history.

(56) References Cited

U.S. PATENT DOCUMENTS

| | | | |
|---|---|---|---|
| 2003/0153971 A1 | 8/2003 | Chandrasekaran | |
| 2004/0117001 A1 | 6/2004 | Pelton | |
| 2005/0131520 A1* | 6/2005 | Zilla | A61F 2/06 623/1.13 |
| 2006/0157159 A1* | 7/2006 | Yeung | A61L 27/06 148/239 |
| 2006/0276875 A1 | 12/2006 | Stinson et al. | |
| 2008/0195196 A1* | 8/2008 | Asgari | A61F 2/856 623/1.39 |
| 2009/0076588 A1* | 3/2009 | Weber | A61F 2/90 623/1.15 |
| 2009/0264975 A1* | 10/2009 | Flanagan | A61L 29/16 623/1.2 |
| 2010/0185271 A1* | 7/2010 | Zhang | A61F 2/915 623/1.11 |
| 2011/0166640 A1* | 7/2011 | Leewood | A61F 2/90 623/1.15 |

FOREIGN PATENT DOCUMENTS

| | | |
|---|---|---|
| DE | 60310686 | 4/2007 |
| EP | 1522605 | * 10/2004 |

OTHER PUBLICATIONS

German Office Action dated Sep. 3, 2013 for applicant's German patent application DE 10 2013 101 334.1.
European Search Report dated Jul. 11, 2014 for applicant's European patent application EP 14154280.3.
C. Trepanier, et al., "Effect of medication of oxide layer of NiTi stent corrosion resistance." Journal of Biomedical Materials Research, vol. 43, No. 4; Dec. 1, 1998, pp. 443-440.
Neelakantan L, et al.; "Selective surface oxidation and nitridation of NiTi shape memory alloys by reduction annealing"; Corrosion Science, Oxford UK, vol. 51, No. 3; Mar. 1, 2009, pp. 635-641.
Y. Cheng, et al.; "Surface characterization and mechanical proprty of TiN/Ti-coated NiTi alloy by PIIID"; Surface and Coatings technology, vol. 201, No. 15; Aug. 27, 2006; pp. 6869-6873.
Oxford Dictionary, Definition of coil, retrieved Jan. 21, 2015.
File History of applicant's U.S. Appl. No. 14/177,470, retrieved Jun. 1, 2016.

* cited by examiner

Untreated Comparison Sample

Fig. 8

Wire Manufactured According to Invention

INTRAVASCULAR FUNCTIONAL ELEMENT AND SYSTEM FOR SUCH A FUNCTIONAL ELEMENT

CROSS-REFERENCE TO RELATED APPLICATIONS

This application claims priority to German patent application DE 10 2013 101 337.6 filed on Feb. 11, 2013 and which is hereby incorporated by reference in its entirety for all purposes.

BACKGROUND OF THE INVENTION

Field of the Invention

The invention relates to an intravascular functional element, especially a stent, and to a system with such a functional element.

Discussion of the Background of the Invention

In medical technology, stents are usually produced by laser methods. However, braids of Nitinol wires are also used for implants (e.g. stents or occluders). In contrast to stents produced by laser methods, the wires of wire braids slide over one another and therefore permit good shape adaptation of the stent structures. In principle, (vascular) implants may be manufactured from semifinished materials such as sheet, precision tubes or wires.

For example, US 2004/0117001 A1 describes a method for production of a stent from Nitinol. One objective of US 2004/0117001 A1 consists in reducing the nickel content in a near-surface layer in order to prevent nickel from being released from the layer, since thereby the biocompatibility of the stent is impaired. A laser method is proposed for production of the stent. After a cold-working step, the stent is heat-treated and then electropolished at temperatures below 20° C. For thermal oxidation, the stent is exposed to superheated steam at a temperature of 150° C. for 12 h. Thereby an oxidic surface with an Ni content of less than 2 wt % in a layer depth of 10 nm is supposedly obtainable.

The known method has the disadvantage that the oxide layer that can be produced therewith on implants consisting of wire braids wears rapidly. For braids, it is important that the contact surfaces of the wires touching one another have low friction, precisely considering that the implanted braids are continuously exposed to pulsatile vessel movements and the wires therefore move relative to one another. Above and beyond this, a low coefficient of friction of the wire surfaces is important for good mobility of the implant in an introducing catheter.

One object of the invention is to provide an intravascular functional element, especially a stent, with improved wear and friction properties and good biocompatibility. A further object of the invention is to provide a system with such a functional element.

SUMMARY OF THE INVENTION

This object is achieved with respect to the functional element by present invention and with respect to the system by present invention.

In particular, the object is achieved by an intravascular functional element with a tubular grid structure that has a wire or several wires respectively of an alloy with nickel and titanium as alloying elements. A mixed oxide layer with a layer thickness of 15 nm to 100 nm and containing $TiO_2$ and at least one nitride, especially titanium oxynitride and/or titanium nitride, is formed on the surface of the wire or on the surface of the wires. The grid structure forms cells of mutually crossing wires or wire segments of the wire in longitudinal direction and in circumferential direction respectively. In circumferential direction of the grid structure there are disposed at least 6 cells, especially at least 12 cells, especially at least 16 cells, especially at least 24 cells, especially at least 36 cells, especially at least 48 cells. For each of the lower limits mentioned in the foregoing, the angle α between the wire segments or wires and a longitudinal axis oriented at least in portions in longitudinal direction of the grid structure is respectively at least 45°, especially at least 50°, especially at least 55°, especially at least 60°, especially at least 65°, especially at least 70°, especially at least 75°.

The grid structure may be a braid, in which the wire segments of the wire or of the wires are braided with one another. In the braid, the angle α corresponds to a lay angle α.

The upper limit of the number of cells over the circumference may be 48 cells. The upper limit of the angle α may be 75°.

The number of cells over the circumference is defined by the number of wires or the number of wire segments forming the grid structure. The number of wires or the number of wire segments is determined in an imaginary surface intersecting the grid structure perpendicular to its longitudinal axis. Thus the intersecting surface is oriented in radial direction relative to the tubular grid structure. The number of points of intersection of wires in the intersecting surface corresponds to the number of wires, especially individual wires, or to the number of wire segments of the grid structure. In general, twice as many wires or wire segments are present as cells, and a first half of the wires or wire segments is oriented in a first spiral direction and a second half of the wires or wire segments is oriented in a second spiral direction opposite the first spiral direction, so that the wires or wire segments cross one another and form cells.

For example, 6 cells are formed over the circumference by 12 wires or wire segments, of which 6 wires or wire segments circle in clockwise direction and 6 wires or wire segments circle in counterclockwise direction.

The grid structure may be formed from several individual wires that run without reversal at the two axial ends of the grid structure, i.e. respectively have free or open wire ends, and that cross one another and in particular are braided for formation of the cells. It is also possible that the grid structure is formed from a single individual wire, which is reversed at the two axial ends of the grid structure, thus forming respective loops there. The cells are formed by wire segments or wire portions of the individual wire, which run in different spiral directions over the circumference of the functional element and cross one another and in particular are braided for formation of the cells. Furthermore, the grid structure may be formed from several individual wires, which are reversed at least at one axial end of the grid structure and form mutually crossing, especially braided wire segments. In this way this same number of cells over the circumference can be formed in various functional elements by different numbers of individual elements, depending on how many individual wires are reversed at one or at both axial ends of the grid structure. When the grid structure is formed by a single individual wire that is reversed multiple times, the number of cells over the circumference should be limited to a maximum of 16 cells, since otherwise the production of the grid structure would be very time-consuming.

According to the invention, the angle α, especially the lay angle α, at least in portions is ≥45°, preferably ≥50°, preferably ≥55°, preferably ≥60°, preferably ≥65°, preferably ≥70°, preferably ≥75°, especially at most 75°. The flexibility of the braid increases with increasing lay angle.

In this connection the lay angle relates to the resting condition of the functional element (in the expanded condition). The determination of the lay angle is therefore carried out in the relaxed condition without any action of external forces. As an example, this condition may correspond to the as-produced condition. For determination of the lay angle, the functional element is aligned straight in axial direction. In this connection, that angle formed between a wire and a perpendicular projection of the axis of rotation onto the plane tangential to the circumference of the grid structure or of the braid is defined as the lay angle. The axis of rotation corresponds to the longitudinal axis of the braid or of the grid structure.

Specifically, it is disclosed that, in the case of 6 or more cells, the angle α between the wire segments or wires and a longitudinal axis oriented at least in portions in longitudinal direction of the grid structure is at least 45°, especially at least 50°, especially at least 55°, especially at least 60°, especially at least 65°, especially at least 70°, especially at least 75°. In the case of 12 or more cells, the angle α between the wire segments or wires and a longitudinal axis oriented at least in portions in longitudinal direction of the grid structure is at least 45°, especially at least 50°, especially at least 55°, especially at least 60°, especially at least 65°, especially at least 70°, especially at least 75°. In the case of 16 or more cells, the angle α between the wire segments or wires and a longitudinal axis oriented at least in portions in longitudinal direction of the grid structure is at least 45°, especially at least 50°, especially at least 55°, especially at least 60°, especially at least 65°, especially at least 70°, especially at least 75°. In the case of 24 or more cells, the angle α between the wire segments or wires and a longitudinal axis oriented at least in portions in longitudinal direction of the grid structure is at least 45°, especially at least 50°, especially at least 55°, especially at least 60°, especially at least 65°, especially at least 70°, especially at least 75°. In the case of 36 or more cells, especially of 40 cells, the angle α between the wire segments or wires and a longitudinal axis oriented at least in portions in longitudinal direction of the grid structure is at least 45°, especially at least 50°, especially at least 55°, especially at least 60°, especially at least 65°, especially at least 70°, especially at least 75°. In the case of 48 or more cells, the angle α between the wire segments or wires and a longitudinal axis oriented at least in portions in longitudinal direction of the grid structure is at least 45°, especially at least 50°, especially at least 55°, especially at least 60°, especially at least 65°, especially at least 70°, especially at least 75°.

The wire cross section is not limited to any particular shape. The cross-sectional shape of the wire may be round, especially circular or elliptical, or polygonal or other shape. The functional element may form a braid, such as a stent, that is tubular at least in portions but in particular is completely tubular. Other applications, such as occluders, flow diverters, filters or thrombectomy devices, are possible.

The invention has several advantages.

The oxide layer formed on the wire surface is low in nickel and contains $TiO_2$, whereby the corrosion behavior and the biocompatibility of the implant are improved. The formation of the oxide layer as a mixed oxide layer, in which at least one nitride is present, especially titanium nitride and/or titanium oxynitride, increases the layer hardness, whereby the wear of the functional element, especially of the implant, is reduced when it is subjected to stress in the vessel. This advantage is noticeable in particular for braids, such as braided stents, which have a large number of wires with many crossing and contact points. Since friction occurs at every crossing and contact point due to the movement of the wires relative to one another, the reduction of wear due to the hard and smooth surface of the wires is particularly noticeable.

The reduced coefficient of friction of the surface of the functional element, especially of the implant, leads to better sliding behavior in the catheter. The good sliding properties act on the one hand between the wires themselves, whereby the crimpability, i.e. the ability of the functional element to be compressed, is improved. As a result, even very fine-meshed implants having a large number of wires, for example flow diverters, can be compressed to very small diameters, so that, for example, aneurysms in narrow vessels can be reached and treated with the implant.

On the other hand, the good sliding properties act between the wires and the inside wall of the catheter. The resulting reduced pushing force necessary to move the functional element, especially an implant, in the catheter increases the safety, since the risk of blockage and of damage to the functional element, especially an implant, in the catheter is reduced. The same is true for introducer systems, in which introduction of the functional element is achieved not by movement of the functional element itself but instead by a relative movement between part of the introducer system and the functional element.

On the whole, the quality of the functional element, especially of the implant, is improved, for example in terms of compliance in the vessel.

The layer thickness of 15 nm to 100 nm has the advantage that the wear resistance is improved compared with a wire that has been merely electropolished. The natural oxide layer, which is formed, after electropolishing, has a layer thickness of approximately 3 to 5 nm, which is why the layer can be easily rubbed off. The layer thickness increased according to the invention, together with the nitriding of the oxide layer, improves the abrasion resistance.

Compared with conventional oxide layers that form with a thickness of more than 200 nm on NiTi wires during wire manufacture, the inventive mixed oxide layer is more protective against the escape of nickel ions, as is demonstrated, for example, by the good corrosion behavior of the layer. The invention therefore unites the good protective properties of a very thin oxide layer with the good abrasion resistance of a relatively thick layer as well as with good sliding properties.

Advantageously the layer thickness is at least 30 nm, especially at least 35 nm, especially at least 40 nm, especially at least 45 nm, especially at least 50 nm, especially at least 55 nm. The abrasion resistance is further improved with the increase of the lower limit of the layer-thickness range.

When the layer thickness is at most 95 nm, especially at most 90 nm, especially at most 85 nm, especially at most 80 nm, especially at most 75 nm, especially at most 70 nm, especially at most 65 nm, especially at most 60 nm, the protective properties of the layer are improved by the reduction of the upper limit of the layer thickness range. Moreover, the risk is less that layer components will be dissolved from the wire surface or that the layer will become brittle—especially during deformations of the wires.

The values cited in the foregoing for the lower limit and the upper limit may be combined respectively with one another, in order to achieve a selective improvement of the respective layer properties. For example, the lower limit for the above maximum values may be 30 nm. A particularly advantageous range of the layer thickness is from 20 nm to 90 nm, especially from 30 nm to 90 nm, especially from 40 nm to 80 nm, especially from 50 nm to 70 nm.

The wire braid may have (in the expanded condition) an outside diameter of ≤7 mm, preferably ≤6 mm, even more preferably ≤5 mm, even more preferably ≤4.5 mm, even more preferably ≤4.0 mm, even more preferably ≤3.5 mm. Particularly preferably, an upper limit of the diameter is ≤6 mm.

At least one wire of the wire braid (preferably several or all wires of the wire braid) may have a diameter of ≤120 μm, ≤90 μm, preferably ≤76 μm, even more preferably ≤51 μm, even more preferably ≤40 μm, even more preferably ≤35 μm, even more preferably ≤25 μm. The lower limit may be 20 μm. Such a wire or such a wire braid is particularly simple to handle and can be introduced easily into the body of the patient. By the respective "diameter", there will be understood (here and in the following) the maximum diameter (in radial direction).

At the distal axial end, the wire braid may have closed end loops. For formation of the end loops, the wire is guided out of the braid, reversed and guided back into the braid. The distal end loops improve the pushing behavior in the catheter. The proximal axial end is formed by free wire ends, which may be joined or arranged loosely in the zone of the crossings near the end. Alternatively, the braid may be formed from a single individual wire, which forms closed end loops at the proximal and distal ends.

The functional element, especially an implant, especially a stent, may be constructed in such a way that an effect of the pushing force is at most 1.5 N, preferably at most 1.3 N, preferably at most 1.1 N, preferably at most 0.9 N, preferably at most 0.8 N, preferably at most 0.7 N, preferably at most 0.6 N, preferably at most 0.5 N per 10 mm length (in the expanded condition of the implant or stent), for a catheter inside diameter of ≤0.8 mm, preferably ≤0.7 mm, more preferably ≤0.6 mm, even more preferably ≤0.5 mm, even more preferably ≤0.4 mm.

The pushing force is that force which must be overcome in order to move the implant, especially the stent, inside a catheter or tube with an inside diameter as specified hereinabove. The upper limits of the force are valid in particular for a braid with at least or exactly 40 wires and/or wire segments, especially with at least or exactly 48 wires and/or wire segments and a wire diameter of at least or exactly 35 μm or at least or exactly 40 μm.

This wire diameter may be at least or exactly 30 μm, especially at least or exactly 35 μm, especially at least or exactly 40 μm. The total diameter of the implant may be at most or exactly 6 mm, especially at most or exactly 5.5 mm, especially at most or exactly 5 mm, especially at most or exactly 4.5 mm, especially at most or exactly 4 mm.

The functional element, especially an implant, described hereinabove may be part of a system comprising the functional element as well as a catheter, wherein a catheter inside diameter is preferably ≤0.8 mm, more preferably ≤0.7 mm, even more preferably ≤0.6 mm, even more preferably ≤0.5 mm, even more preferably ≤0.4 mm. In this connection, the use of a functional element (produced) as described hereinabove, especially an implant for a catheter and/or as a stent, is independently disclosed and claimed.

The wire braid or in general wire structure may be made at least partly from composite wires, wherein an inner core of the wire consists of a radiologically visible material, such as platinum or tantalum.

In a preferred embodiment, the peak of the oxygen concentration in the mixed oxide layer forms a plateau. For example, the plateau may be formed in a layer depth of 5 nm to 50 nm, especially from 10 nm to 40 nm, especially from 15 nm to 30 nm. In this case the total layer thickness is at least approximately 60 nm. As a reason for the plateau, it is assumed that the oxygen combines preferentially with nitrogen outwardly toward the layer surface and with titanium inwardly toward the wire material.

The ratio of intensities between nitrogen and oxygen (N/O) is at most 1:2.0, especially from 1:2.5 to 1:10 in the region of the oxygen plateau, and decreases toward the wire metal body, the intensities being determined respectively by Auger electron spectroscopy (AES) in the depth profile through the mixed oxide layer. At the layer surface, the ratio of intensities between nitrogen and oxygen (N/O) is at most approximately 1:2.0, especially approximately 1:2.5. The ratio of 1:2.0 lies in the immediate boundary layer of the layer surface (approximately 5-10 nm), the ratio of 1:6 at a layer thickness of approximately 20-25 nm, for example, and the ratio of 1:10 at a layer thickness of approximately 35-40 nm, for example. In general, therefore, the N/O ratio decreases toward the wire metal body.

Since oxygen is present not in the wire material but only in the layer, the nitrogen intensity of the mixed oxide layer is expressed relative to the oxygen intensity. Thereby the nitrogen content of the mixed oxide layer in the zone of the layer thickness can be characterized indirectly.

AES is a known technique for analysis of the elements of a material present in a near-surface layer. Because of successive ablation of the layer by sputtering, a depth profile of the element distribution in the layer is generated by AES analysis of the respectively exposed layer surface and is used for characterization of the nitrogen content relative to the oxygen content as well as for detection of the concentration profile of the other elements, such as Ni and Ti. The measured intensity of the respective element is obtained in the known way from the Auger electrons emitted by electron bombardment during the AES analysis.

Preferably the nitrogen is present in the mixed oxide layer down to a depth of $2/6$, especially to $3/6$, especially to $4/6$ of the total thickness of the mixed oxide layer, including the first oxide layer. In absolute values, the nitrogen-containing boundary layer extends down to a layer depth of 10 nm, especially 20 nm, especially 30 nm, especially 40 nm, especially 50 nm, for example in a mixed oxide layer with a total thickness of approximately 60 nm. Thereby a hard boundary layer of the mixed oxide layer is generated and the abrasion resistance is improved.

For production of the intravascular functional element, there is used a method in which a metal body of the wire is prepared with a metallic surface. Then a first oxide layer is formed on the metallic surface of the metal body. For thermal formation of a second mixed oxide layer on the first oxide layer, a heat treatment of the wire is carried out in a nitrogen-containing salt bath, wherein the total layer thickness is 15 nm to 100 nm and the mixed oxide layer contains $TiO_2$ and at least one nitride, especially titanium oxynitride and/or titanium nitride.

For preparation of the wire metal body with a metallic surface, a pretreatment is carried out in which an oxide layer usually present on the wire surface is removed. This oxide layer, with a thickness of 0.2 μm to 5 μm, is formed during wire manufacture, when a heat treatment is applied to adjust the material characteristics of the wire. Various methods, which may be used within the scope of the invention, come into question for removal of the oxide layer, in order to prepare a wire metal body with a metallic surface. The invention is not limited to these methods.

In a preferred embodiment, the above manufacturing-related oxide layer is removed by electropolishing. In this process, metal together with impurities as well as an oxide layer formed naturally on the wire surface is stripped from the wire surface in a way known in itself in an electrolyte bath under the action of current, so that a smooth and homogeneous metallic surface that is substantially oxide-free is obtained after electropolishing.

The wire metal body with a metallic surface may be produced in other ways, for example by chemical or electrochemical or mechanical stripping of the surface layer of the wire. One option for chemical stripping is etching or pickling. In this way the natural oxide layer is removed, exposing the metallic surface of the wire body. The process parameters used for this purpose are known to the person skilled in the art, for example from US 2004/0117001 A1. Microabrasive stripping methods, which may likewise be used in the invention, are also known.

A first oxide layer, on which the second mixed oxide layer is thermally applied, is formed on the metallic surface of the wire metal body. In the simplest case, the formation of the first oxide layer can take place in the form of a natural oxide layer, which is formed when the metallic surface of the wire metal body is exposed to the ambient air. If the pretreatment of the wire is carried out by electropolishing, for example, it has been found that the natural first oxide layer has a thickness of approximately 3 nm to 10 nm.

Preferably the wire for production of a wire structure, i.e. the grid structure, is shaped before the heat treatment, in which case at least one portion, especially several portions of the shaped wire cross over and/or touch one another. The wire structure may comprise, for example, a braid, specifically a braided implant, for example a braided stent, a graft stent, a braded occlusion device or a braided flow diverter. For the braid, meshes bounded by wire crossings are formed in the known way. The braid may be formed from a single wire or from several wires. Conventional braiding techniques may be used for this purpose. In the zone of the wire crossings, the wires or portions may contact one another or be spaced apart from one another.

The preferred formation of the wire structure after electropolishing of the wire or in general before the heat treatment for formation of the mixed oxide layer has the advantage that the wire is treated in the straight condition in the solution used for electropolishing, i.e. without wire crossings or contact points. In this way the solution is able to wet the wire surface uniformly in the entire surface zone. Shadowing in the zone of wire crossings and/or contact points is avoided, since the formation of the wire structure takes place only after electropolishing. Because of the uniform ablation achieved thereby during electropolishing, the prerequisite for formation of a homogeneous oxide layer with the most constant thickness possible is created in the subsequent process steps. The grid structure or the braid is therefore characterized by the fact that the diameter remains constant or almost constant along the wire, even in the zone of each crossing.

Specifically, the oxide layer present after wire manufacture is removed along with impurities by the electropolishing, and so a substantially bright metal surface of the wire remains at first after electropolishing. The wire is removed from the solution and exposed to the ambient air. Because of the contact with air, a natural oxide layer with a thickness of approximately 5 nm forms on the wire surface. This oxide layer is homogeneous and has a substantially constant thickness. It consists mainly of $TiO_2$. The Ni content in the oxide layer decreases rapidly toward the surface, which is substantially nickel-free.

After the wire has been reshaped to a wire structure with at least one crossing, thermal oxidation is carried out in the salt bath. Thereby the surface is modified after electropolishing, and in particular it is passivated and hardened. Since the oxide layer formed naturally after electropolishing is low in nickel or even nickel-free at least in the near-surface boundary zone and thus acts as a barrier to the metal interface of the wire, the thermally formed oxide layer also has only a low Ni content or is low in nickel or even nickel-free, at least in the near-surface boundary zone. By virtue of the subsequent heat treatment in the nitrogen-containing salt bath, a dense mixed oxide layer containing $TiO_2$ is generated on the naturally formed oxide layer. In addition, the mixed oxide layer contains proportions of nitrogen combined as titanium oxynitride and/or titanium nitride. Titanium oxynitride and/or titanium nitride is obtained from the salt bath, for example by using an alkali metal-nitrogen salt, especially potassium nitrate or sodium nitrite, or a mixture of potassium nitrate and sodium nitrite. The thermally formed nitride, especially titanium oxynitride and/or titanium nitride, acts as a hard material, which increases the layer hardness and improves the wear and friction behavior of the functional element, especially an implant.

In contrast to the prior art, electropolishing is therefore carried out at first in this embodiment and is followed by a heat treatment in the salt bath. The net result is that oxidation subsequent to the electrochemical polishing process is achieved by the thermal (inert) salt-bath treatment. Thereby very dense as well as low-friction and wear-resistant oxide layers can be produced, with thicknesses that may exceed 10 nm. Moreover, particularly favorable physical properties, for example with respect to radial force and fatigue behavior, physicochemical properties, especially with respect to nickel release and corrosion behavior, and biological interface characteristics, for example thrombogenicity, of functional elements, especially implants such as stents, can be achieved relatively accurately and simply. Thereby the surface behavior and the biocompatibility can be significantly improved.

The invention is not limited to a special NiTi alloy. To the contrary, it is generally possible to use NiTi alloys, common to medical technology, from which intravascular functional elements, especially implants, the surfaces of which must be protected by an oxide layer, are produced.

Examples of alloys are various binary compounds based on Ni, such as, for example, NiTi alloys, especially Nitinol (Ni 55 wt %, Ti 45 wt %), or various ternary compounds, such as, for example, NiTiFe or NiTiNb or NiTiCr, or quaternary alloys such as NiTiCoCr.

The wire may contain at least 5 wt %, preferably at least 10 wt %, preferably at least 20 wt %, preferably at least 40 wt % nickel. The wire may further preferably contain at most 80 wt %, preferably at most 60 wt %, preferably at most 55 wt %, preferably at most 50 wt % nickel. The titanium content may preferably be at least 10 wt %, preferably at least 30 wt %, preferably at least 40 wt %, preferably at least 50 wt %. A surface limit for the titanium content may be 90 wt %, preferably 80 wt %, preferably 65 wt %, preferably 60 wt %, preferably 55 wt %.

Preferably the exposure to heat takes place (at least partly) simultaneously with the immersion in the salt bath, and further preferably exposure to heat takes place at least during 10%, further preferably at least during 30%, even further preferably at least 50%, even further preferably at least 90% of the time of immersion in the salt bath. An additional heat treatment may be carried out before or after immersion in the salt bath. Preferably, however, heat treatment is carried out only during immersion in the salt bath.

In one embodiment, the heat treatment in the salt bath is carried out in at least two steps, wherein the second step is carried out after the introduction of functional means, such as radiologically visible markings, and/or after joining processes. It has been found that, if the mixed oxide layer is damaged by mechanical or thermal joining processes such as the fixation of radiologically visible materials, a second heat treatment is able to anneal out these defects. The treatment time, especially of the first heat-treatment step, is preferably at least 1 min, preferably at least 2 min and/or preferably at most 8 min, preferably at most 7 min, preferably at most 6 min, preferably at most 5 min, preferably at most 4 min, preferably at most 3 min. The duration of the second heat-treatment step may be at least 50% shorter than the duration of the first heat-treatment step. Preferably the duration of the first heat-treatment step is approximately 2 min to 4 min and the duration of the ensuing second heat-treatment step is approximately 20 s to 60 s.

The upper temperature limit of the heat treatment in the salt bath is preferably 550° C., especially 540° C., especially 530° C., especially 520° C. The lower limit can be 400° C., especially 420° C., especially 440° C., especially 460° C., especially 480° C.

The implant is preferably a braided stent, but may also be a different implant, for example a flow diverter or a stent graft or an intravascular occlusion device or an intravascular coil.

The nickel content in the mixed oxide layer is preferably less than 6 wt %, even more preferably less than 3 wt %, even more preferably less than 2 wt % respectively at least to a layer depth of 30% of the total thickness of the mixed oxide layer, starting from the layer surface, especially to a layer depth of 50% of the total thickness of the mixed oxide layer, starting from the layer surface. Specifically, the low-nickel layer zone may extend to a depth of 20 nm to 40 nm in a layer thickness of 60 nm to 100 nm. The surface of this mixed oxide layer may consist predominantly of $TiO_2$.

A contact angle, i.e. the wetting angle of the surface of the implant when wetted with distilled water, is preferably smaller than 90°, more preferably less than 80°, even more preferably less than 75°, and/or at least 30°, preferably at least 60°. At such a contact angle (wetting angle), the biocompatibility of the implant is relatively high. Furthermore, such a contact angle may be adjusted particularly simply by the sequence of manufacturing steps described hereinabove.

In a further embodiment, a salt of the salt bath is an alkali metal-nitrogen salt, preferably a potassium-nitrogen salt and/or sodium-nitrogen salt, especially potassium nitrate and/or sodium nitrite, especially a mixture of potassium nitrate and sodium nitrite. Further salts may (but do not have to) be present. It has been found that a mixed oxide layer, especially containing titanium oxynitride, which is characterized by favorable surface properties (low roughness) and high biocompatibility, can be obtained by such a salt bath containing nitrate and/or nitrite.

It has been found that dense and protective mixed oxide layers are obtained, as shown by the improved corrosion behavior of the implants, when the content of potassium nitrate is greater than the content of sodium nitrite. Specifically, the salt bath may contain the following components:
30-40 wt % $KNO_3$
25-35 wt % $NaNO_2$
rest usual carbon compounds and impurities,
subject to the condition that the content of potassium nitrate is greater than the content of sodium nitrite. The carbon compounds are compounds known to the person skilled in the art in connection with salt baths for heat treatment. Preferably the content of potassium nitrate is 32-38 wt %, especially 34-36 wt %. The content of sodium nitrite may be 26-33 wt %, especially 27-30 wt %.

It is assumed that the high content of $KNO_3$, which has a higher decomposition temperature than $NaNO_2$, favors nitrogen enrichment and oxidation.

The mixed oxide layer may contain at least 10 wt %, more preferably at least 20 wt %, more preferably at least 30 wt %, more preferably at least 40 wt %, more preferably at least 50 wt % titanium oxynitride and/or titanium nitride.

The wire may be an endless wire, which, for example, is wound on a spool or by a spool. Thereby not only is the production method—especially the electropolishing—simplified but also an implant that is easy to handle is obtained.

It is particularly preferred when the braid is formed only after the electropolishing or in general before the heat treatment. In this special embodiment it has been recognized that the crossing points of wire braids (which are known in themselves) usually represent a weakness in the prior art, since the medium for the electropolishing cannot act sufficiently in this zone of overlapping of the wires because of shadowing effects. By the fact that a braid is formed only after the electropolishing, the surface of the wire braid is entirely homogeneous and has relatively good biocompatibility. When the wire or the wires is or are electropolished before braiding, a relatively uniform wire diameter is obtained, thus positively influencing the mechanics of the functional element, especially an implant, and the compliance. If the electropolishing were to be carried out only after braiding, a reduction of the ablation during electropolishing would be suffered in the zone of the wire crossings, where the electropolishing solution is not in sufficiently good contact with the wires. This would lead to irregular wire diameters or uneven development of the surface properties.

Preferably the surface layer has a nickel content of less than 6 wt %. Preferably the surface layer has a nickel content of less than 3 wt %, even more preferably of less than 2 wt %.

On the whole, by virtue of the actions described hereinabove, especially the nickel release of implants is minimized, the radial force of medical implants (e.g. of Nitinol) is optimized, the material fatigue behavior of the implant (e.g. of Nitinol) is improved, the corrosion behavior of the implant (e.g. of Nitinol) is improved, the surface roughness of the implant (e.g. of Nitinol) is lessened and the thrombogenicity of medical implants (e.g. of Nitinol) is improved. Moreover, the aggregation of proteins and other blood components, which may lead to thrombosis, is extremely low (by virtue of the low or zero porosity). Instead of braids, it is possible in general to use wire structures having at least one contact point between two wires (devices, for example, that are produced by wire forming or other textile processes).

If a parameter (e.g. the layer thickness) were to vary, the respective maximum value or the (geometric) mean value may be intended.

BRIEF DESCRIPTION OF THE DRAWINGS

The invention will be explained in more detail hereinafter on the basis of exemplary embodiments with reference to the attached schematic drawings, wherein:

FIG. 7 shows a corrosion curve (1586-170-04) of a functional element according to an inventive exemplary embodiment;

DETAILED DESCRIPTION OF THE INVENTION

Figure 1:
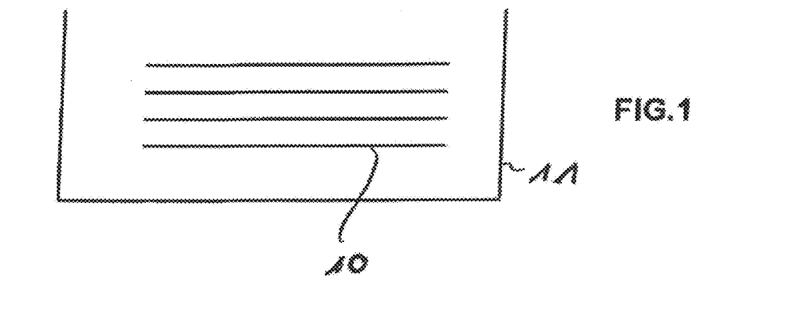
FIG. 1 shows several wires in an electropolishing bath.

FIG. 1 shows a first step for the production of a stent. Several wires 10 (four wires in the schematic drawing) are immersed in an electropolishing bath 11 of an electrolyte. This step may be carried out as in US 2004/0117001 A1, except for the timing sequence.

Figure 2:
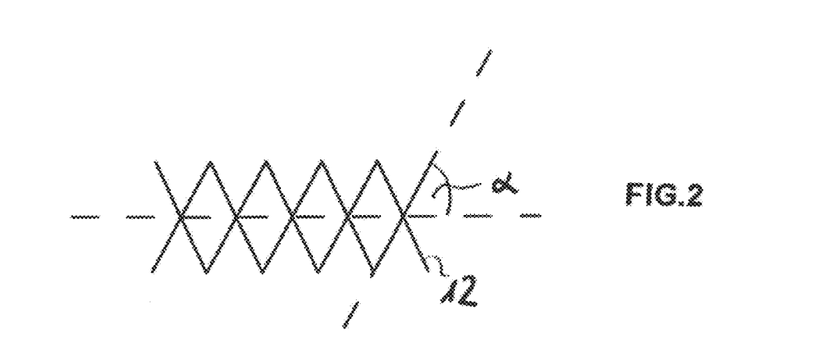
FIG. 2 shows a schematic braid of several wires.
Figure 3:
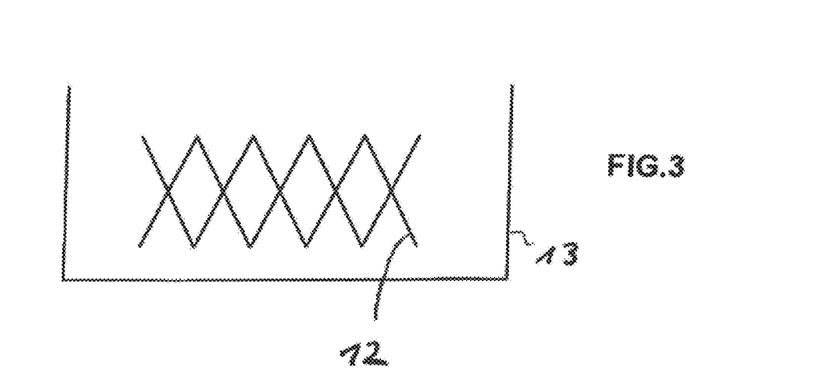
FIG. 3 shows the braid according to FIG. 2 in a salt bath.

FIG. 2 shows (schematically) a braid 12 of wires 10. This braid 12 is illustrated in the expanded condition, so that the entire circumferential surface of the braid 12 is shown in the drawing plane. After the braiding step, braid 12 is immersed and heat-treated in a salt bath 13 (see FIG. 3). In salt bath 13, braid 12 or the stent receives its final structure, including the passivated surface. This does not rule out the possibility that still further processing steps will be carried out.

Example

The invention will be explained by means of an example of a functional element produced from a binary NiTi alloy, such as Nitinol. Other NiTi-containing alloys are possible. In this case the modification of the surface is represented by the thermal treatment in the salt bath, which treatment is responsible for adjusting the nitrogen concentration in the $TiO_2$ mixed oxide layer. The basic component of the functional element, namely the wire, is electropolished in the first step. The electropolishing may be carried out as is usual in the prior art, for example at a temperature T<20° C., using a methanolic sulfuric acid solution. A homogeneous natural oxide layer with a layer thickness of approximately 5 nm is spontaneously formed on the electropolished wire upon contact with the ambient air.

In the second step, a functional element, a stent, is braided using the electropolished wire.

In the third step, the functional element is heat-treated in the salt bath in order to increase the layer thickness. For this purpose there is used a salt-bath composition consisting of the following components:

approximately 35-36 wt % $KNO_3$
approximately 27-29 wt % $NaNO_2$
rest usual carbon compounds and impurities.

It has been found that good results may be achieved when the content of potassium nitrate is greater than the content of sodium nitrite in the salt bath.

The process temperatures are approximately 490° C. to 510° C. In the first treatment step, the functional element is immersed for approximately 2 to 3 minutes in the salt bath. Formation of the oxide layer takes place during this time. The treatment time in the second step is approximately 30 sec or shorter.

Measuring Technique

Figure 4:
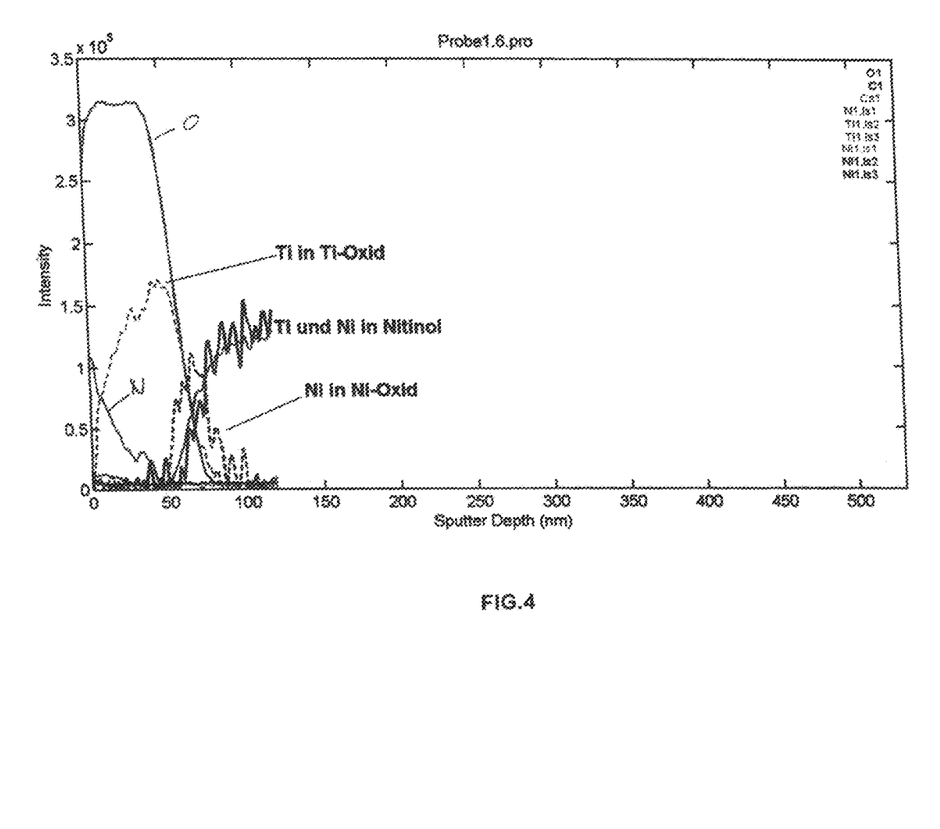
FIG. 4 shows a depth profile of a mixed oxide layer of a functional element according to an inventive exemplary embodiment with a layer thickness of approximately 60 nm (Probe1.6pro)
Figure 5:
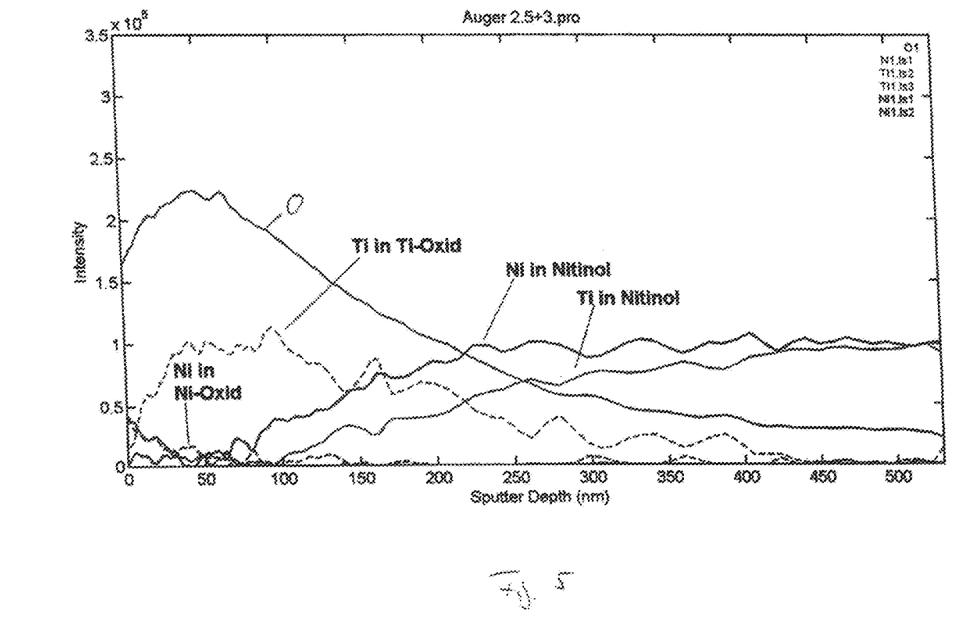
FIG. 5 shows a depth profile of a mixed oxide layer of a functional element according to an comparison example with a layer thickness of approximately 220 nm (Auger2.5+3.pro)

The measurements to determine the AES depth profile according to FIGS. 4 and 5 were made with the following parameters:

Primary electron energy (excitation): 5 keV
Beam current: 20 nA
Electron beam raster (analyzed zone): 20 μm×2 μm
Ion beam energy: 3 keV (FIG. 4, Probe1.6.pro, treated in each case)
Beam current: 2 μA
Ablation rate: 59.3 nm/min
Ion beam raster: 0.8 mm×0.8 mm
Ion beam energy: 1 keV (FIG. 5, Auger2.5+3.pro, untreated)
Beam current: 0.5 μA
Ablation rate: 8.24 nm/min
Ion beam raster: 0.8 mm×0.8 mm
Sample angle (between electron beam and normal to the sample): 30°

The following element peaks were used for determination of the intensities:

Ti1: Ti LMM at 390 eV
Ti2: Ti LMM at 421 eV
N1: N KLL at 389 eV
Ni1: Ni LMM at 849 eV
O1: O KLL at 510 eV

Figure 6:
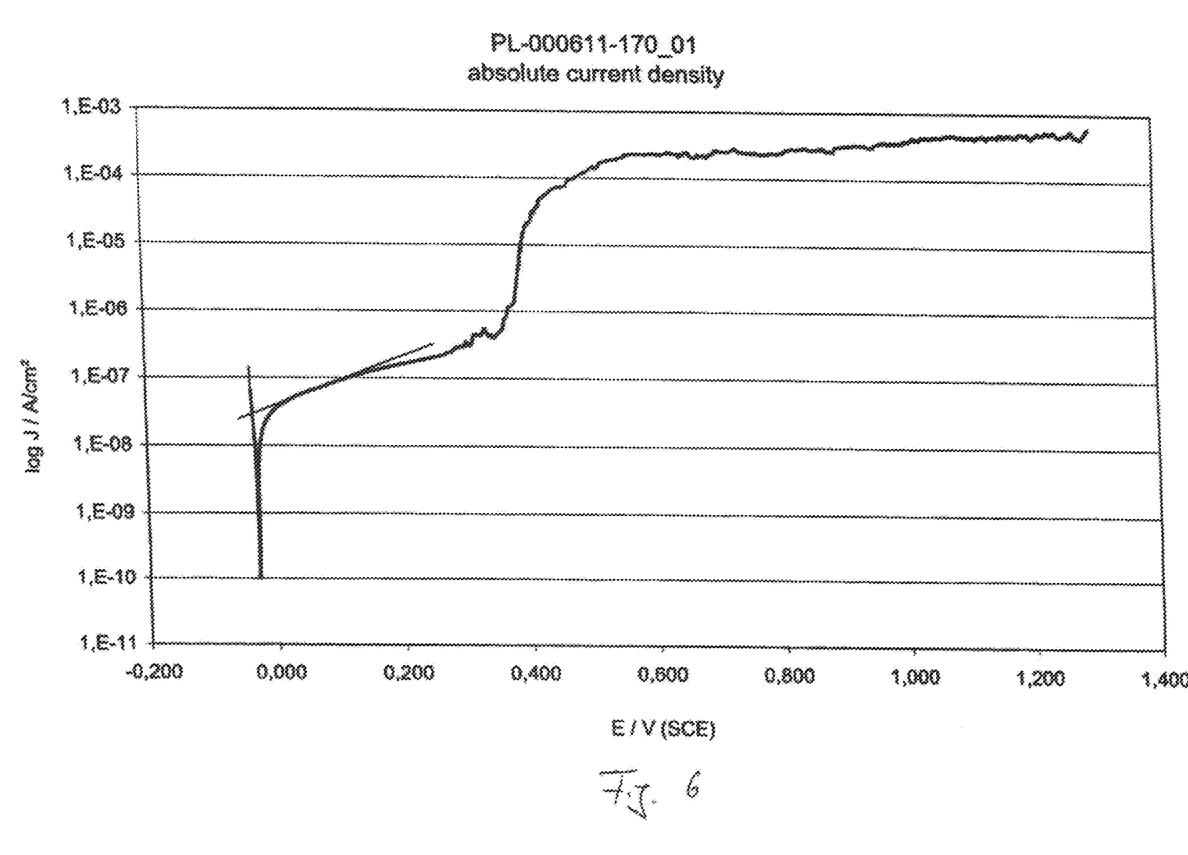
FIG. 6 shows a corrosion curve (0611-170-01) of a functional element as a comparison example, in which a non-electropolished wire is used.

The measurements for the corrosion curves according to FIGS. 6 and 7 were carried out according to ASTM F2129 "Standard Test Method for Conducting Cyclic Potentiodynamic Polarization Measurements to Determine the Corrosion Susceptibility of Small Implant Devices".

Results and Discussion

The depth profile according to FIG. 4, where the sputtering depth is normalized to 500 nm, shows the concentration profile obtained for the layer elements after the process explained in the foregoing has been carried out. In the process, the layer thickness is generally determined from the sputtering parameters. Alternatively to the determination of the layer thickness, 50% of the "peak value" of $TiO_2$ is calculated. Accordingly, the layer has a thickness of approximately 60 nm, which is obtained from the intersection of the oxygen peak and the peak for metallic Ti and Ni. The following peaks are marked in FIG. 4:

Oxygen
Nitrogen
Ti in the titanium oxide
Titanium (metallic titanium)
Ni in the Ni oxide
Ni It is particularly obvious that the oxygen peak has the form of a plateau. The plateau extends over a layer depth between approximately 10 nm and 40 nm. One possible explanation is that the oxygen also combines with nitrogen toward the outer part of the layer and then combines with titanium toward the inner part of the layer. The nitrogen is incorporated as a chemical compound in the layer, and specifically as titanium oxynitride. This follows from the shape of the oxygen signal, which forms a plateau. It may also well be that the nitrogen is additionally present even as titanium nitride. In general, the plateau shape means that the oxygen intensity is zonally constant, especially over a layer depth of at least 10 nm.

In the region of the oxygen plateau, the most obvious ratios N/O of the intensities of nitrogen and oxygen in the layer are approximately 1:3; 1:6; 1:10, where the ratio 1:3 is located in the immediate boundary layer of the outer surface of the layer (approximately 5 nm to 10 nm), the ratio 1:6 at a layer depth of approximately 20 to 25 nm, for example, and the ratio 1:10 at a layer depth of approximately 35 to 40 nm, for example. The ratio at the layer surface is approximately 1:2.5.

From FIG. 4 it is further apparent that a distinct enrichment of Ni oxide is present in the inner part of the layer, in other words close to the metallic wire body. The rest of the layer contains hardly any nickel. In particular, the outer boundary layer is low in nickel. This concentration profile could be imposed by the nitrogen, which may well combine preferentially with oxygen rather than with nickel and thus suppress nickel enrichment in the outer part of the layer.

FIG. 5 shows the depth profile of an untreated sample with an oxide layer thickness of approximately 220 nm (see Ni/O intersection). The investigated oxide layer was formed by the heat treatment during wire manufacture. No treatment was carried out for the sample according to FIG. 5, i.e. the manufacturing-related oxide layer was left on the surface of the wire. FIG. 5 shows that the oxygen profile does not form a plateau. The oxygen intensity increases to approximately 50 nm then decreases. In contrast to the layer according to FIG. 4, moreover, a slight enrichment of nickel oxide is apparent in the near-surface zone of the layer. Enrichment of nickel oxide in the zone of the layer close to the metal body is absent. On the whole, the nitrogen intensity in the layer is significantly lower than in the layer according to FIG. 4.

The protective behavior of the layer is assessed on the basis of the corrosion curves according to FIGS. 6 and 7, from which the electrochemical behavior of the layers and therefore the layer properties of interest, such as the release of nickel ions, for example, can be deduced. In FIGS. 6 and 7, the current density J in A/cm$^2$ is plotted against the voltage E in V (SCE).

FIG. 7 shows the corrosion curve (1586-170-04) of an inventively produced layer, which exhibits a very low corrosion current density ($<1 \times 10^{-8}$ A/cm$^2$). This means that the layer has low permeability for metal ions and therefore exhibits a good protective effect. It is particularly important, as follows from the almost linear increase, that no perforation, i.e. no pitting corrosion occurs. Accordingly the layer properties are excellent.

In contrast to this, as shown in FIG. 6, the corrosion current in the conventionally produced layer is greater than $1 \times 10^{-7}$ A/cm$^2$. Perforations suggestive of the onset of pitting corrosion, i.e., the formation of small holes, can be observed at approximately 400 mV.

Figure 8:
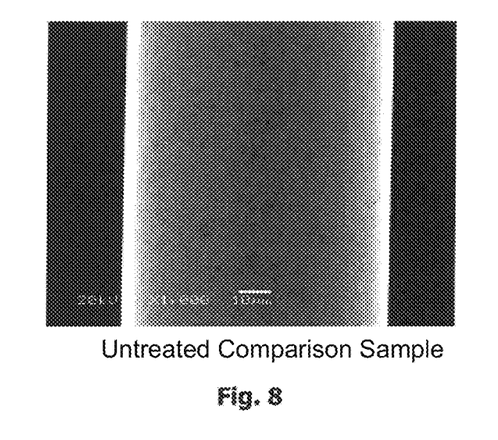
FIG. 8 shows an SEM photograph of an untreated comparison sample.
Figure 9:
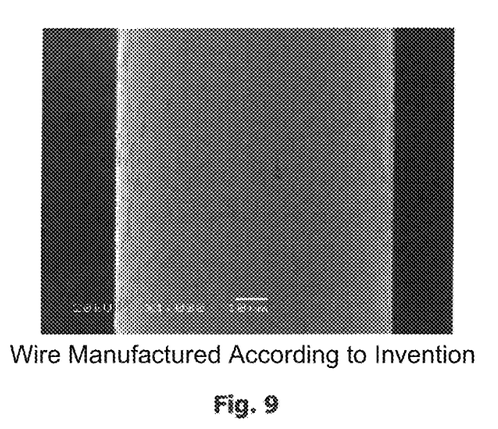
FIG. 9 shows an SEM photograph of a wire surface generated according to an embodiment of the inventive method.

The good surface properties are obvious from the comparison between the surface of an untreated wire having a manufacturing-related oxide layer, illustrated in FIG. 8, and the surface of a wire heat-treated according to the invention, shown in FIG. 9. The oxide layer of the wire according to FIG. 9 is uniformly dense and pore-free.

By means of the inventive method it is possible to produce very corrosion-stable and hard mixed oxide layers, which develop a good protective effect and protect safely against abrasion.

List of Reference Symbols

α Braid angle
10 Wire
11 Electropolishing bath
12 Braid
13 Salt bath

What is claimed is:

1. An intravascular functional element comprising:
   a wire comprising
      a diameter between 30 μm and 120 μm;
      an alloy of nickel and titanium as alloying elements, and
      a plurality of wire segments;
   a mixed oxide layer formed on a surface of the wire, the mixed oxide layer comprising
      a layer thickness from 15 nm to 100 nm,
      TiO$_2$, and
      a nitride, the nitride being a titanium nitride or a titanium oxynitride; and
   a braided structure comprising a plurality of cells and having a longitudinal axis, wherein respective wire segments of the plurality of wire segments cross over each other defining at least one respective cell of the plurality of cells in a longitudinal direction and in a circumferential direction;
   wherein, in the circumferential direction, the braided structure comprises at least 6 cells; and
   wherein an angle between at least one wire segment of the respective wire segments and the longitudinal axis is at least 45°;
   wherein the mixed oxide layer is formed in a zone where the respective wire segments cross over each other.

2. The intravascular functional element of claim 1,
   wherein the braided structure comprises an expanded state,
   wherein the braided structure in the expanded state comprises an outside diameter of 7 mm or less.

3. The intravascular functional element of claim 1,
   wherein the braided structure comprises an expanded state,
   wherein a force pushing the braided structure in the expanded state in a catheter is respectively at most 1.5 N per 10 mm length of the catheter having an inside diameter of 0.8 mm or less.

4. The intravascular functional element of claim 1, wherein the mixed oxide layer is 55 nm or less.

5. The intravascular functional element of claim 1, wherein the mixed oxide layer is 95 nm or less.

6. The intravascular functional element of claim 1,
   wherein an oxygen concentration in the mixed oxide layer forms a plateau.

7. The intravascular functional element of claim 6,
   wherein the wire comprises a wire metal body,
   wherein a ratio of nitrogen intensity and oxygen intensity is 1:2.0 or less in the plateau, and decreases toward the wire metal body, the nitrogen intensity and the oxygen intensity being determined by Auger electron spectroscopy (AES).

8. The intravascular functional element of claim 1, wherein the mixed oxide layer comprises nitrogen, the nitrogen extending from a top surface of the mixed oxide layer to a depth of ⅔ of a total thickness of the mixed oxide layer.

9. The intravascular functional element of claim 1, wherein the mixed oxide layer comprises nickel, the nickel extending from a top surface of the mixed oxide layer to a depth of 30% of a total thickness of the mixed oxide layer and is at most 6% by weight of the mixed oxide layer.

10. The intravascular functional element of claim 1, wherein the wire comprises a wire metal body, wherein the mixed oxide layer comprises an inner zone and an enrichment of nickel oxide in the inner zone adjoining the wire metal body.

11. A functional element according to claim 1, wherein the wire has a diameter of 30 μm.

12. A functional element according to claim 1, wherein the mixed oxide layer is 30 nm or less.

13. A system comprising:
an intravascular functional element comprising
a wire comprising
a diameter between 30 μm and 120 μm;
an alloy of nickel and titanium as alloying elements, and
a plurality of wire segments;
a mixed oxide layer formed on a surface of the wire, the mixed oxide layer comprising
a layer thickness from 15 nm to 100 nm,
$TiO_2$, and
a nitride, the nitride being a titanium nitride or a titanium oxynitride; and
a braided structure comprising a plurality of cells and having a longitudinal axis, wherein respective wire segments of the plurality of wire segments cross over each other defining at least one respective cell of the plurality of cells in a longitudinal direction and in a circumferential direction;
wherein, in the circumferential direction, the braided structure comprises at least 6 cells; and
wherein an angle between at least one wire segment of the respective wire segments and the longitudinal axis is at least 45°; and
a tubular element for receiving the intravascular functional element, the tubular element comprising an inside diameter that ranges from 0.4 mm to 0.8 mm;
wherein the mixed oxide layer is formed in a zone where the respective wire segments cross over each other.

14. The system of claim 13, wherein the braided structure comprises an expanded state, wherein the braided structure in the expanded state comprises an outside diameter of 7 mm or less.

15. An intravascular functional element comprising:
a plurality of wires comprising an alloy of nickel and titanium as alloying elements, each wire of the plurality of wires having a diameter between 30 μm and 120 μm;
a mixed oxide layer formed on a surface of each wire of the plurality of wires, the mixed oxide layer comprising
a layer thickness from 15 nm to 100 nm,
$TiO_2$, and
a nitride, the nitride being a titanium nitride or a titanium oxynitride; and
a braided structure comprising a plurality of cells and having a longitudinal axis, wherein respective wires of the plurality of wires cross over each other defining at least one respective cell of the plurality of cells in a longitudinal direction and in a circumferential direction;
wherein in the circumferential direction the braided structure comprises at least 6 cells; and
wherein an angle between at least one wire of the respective wires and the longitudinal axis is at least 45°;
wherein the mixed oxide layer is formed in a zone where the respective wire segments cross over each other.

16. The intravascular functional element of claim 15, wherein an oxygen concentration in the mixed oxide layer forms a plateau,
wherein the wire comprises a wire metal body, and
wherein a ratio of nitrogen intensity and oxygen intensity is 1:2.0 or less in the plateau, and decreases toward the wire metal body, the nitrogen intensity and the oxygen intensity being determined by Auger electron spectroscopy (AES).

* * * * *